United States Patent [19]

Denny et al.

[11] Patent Number: 5,554,648
[45] Date of Patent: Sep. 10, 1996

[54] COBALT COMPLEXES AS ANTICANCER AGENTS

[75] Inventors: William A. Denny; Brian D. Palmer; David C. Ware; William R. Wilson, all of Auckland, New Zealand

[73] Assignee: Warner Lambert Company, Morris Plains, N.J.

[21] Appl. No.: 263,640

[22] Filed: Jun. 22, 1994

Related U.S. Application Data

[60] Division of Ser. No. 184,413, Jan. 21, 1994, Pat. No. 5,348,977, which is a continuation-in-part of Ser. No. 83,862, Jun. 28, 1993, abandoned, which is a continuation of Ser. No. 825,228, Jan. 24, 1992, abandoned.

[30] Foreign Application Priority Data

Jan. 25, 1991 [NZ] New Zealand .............................. 236906

[51] Int. Cl.$^6$ ..................... A61K 31/295; C07F 15/06
[52] U.S. Cl. .............................................. 514/501; 556/138
[58] Field of Search ................................ 514/501; 556/138

[56] References Cited

U.S. PATENT DOCUMENTS

| | | | |
|---|---|---|---|
| 2,645,653 | 7/1953 | Zerweck et al. | 260/439 |
| 4,189,306 | 2/1980 | Sandy | 44/68 |

OTHER PUBLICATIONS

J. A. Broanhead, "The Reactivity of Hydroxy Groups in Metal Complexes", J. Am. Chem. Soc. 90(16):4480 (1968).

*Primary Examiner*—Porfirio Nazario-Gonzales
*Attorney, Agent, or Firm*—Pennie & Edmonds

[57] ABSTRACT

New cobalt complexes of nitrogen mustard alkylating agents which have been found to have hypoxia-selective antitumor properties and are thereby useful antitumor agents are described.

8 Claims, No Drawings

COBALT COMPLEXES AS ANTICANCER AGENTS

This is a division of application Ser. No. 08/184,413, filed Jan. 21, 1994, now U.S. Pat. No. 5,348,977, issued Sep. 20, 1994, which, in turn, is a continuation-in-part of application Ser. No. 08/083,862, filed Jun. 28, 1993, which, now abandoned, in turn, is a continuation of Ser. No. 07/825,228, filed Jan. 24, 1992, and now abandoned.

BACKGROUND OF THE INVENTION

Nitrogen mustard alkylating agents are an important class of anticancer drugs, which express their cytotoxic and antitumour effects by cross-linking cellular DNA (Garcia et al., Biochem. Pharmacol., 1988, 37, 3189).

We have found that novel cobalt complexes of nitrogen mustard alkylating agents have hypoxia-selective antitumour properties and are therefore useful as antitumour agents.

BRIEF DESCRIPTION OF THE INVENTION

The present invention relates to novel cobalt complexes of nitrogen mustard alkylating agents having hypoxia-selective antitumour properties, to methods of preparing the novel compounds, and to the use of these compounds as antitumour agents.

DETAILED DESCRIPTION OF THE INVENTION

The present invention relates to the class of cobalt complexes represented by the general formulae (I), (II), (III), (IV) and (V) which are useful in the treatment of tumours, and in particular cancers in a patient.

In one aspect, the present invention relates to the class of cobalt complexes represented by the general formulae (I) and (II)

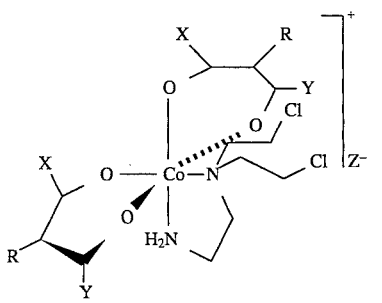

(I)

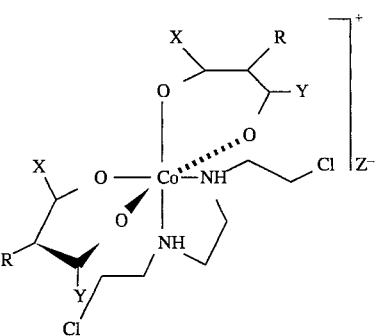

(II)

where X and Y separately represent H, lower alkyl (optionally substituted with hydroxy and/or amino functions) containing from 1 to 6 carbon atoms, or phenyl; R represents H, lower alkyl (optionally substituted with hydroxy and/or amino functions), phenyl (optionally substituted with Me, OQ, CONHQ, and/or NHCOQ, where Q is lower alkyl optionally substituted with hydroxy and/or amino functions and containing from 1 to 6 carbon atoms) or halogen, and $Z^-$ is $Cl^-$, $Br^-$, $I^-$, $ClO_4^-$, $NO_3^-$, $HCO_3^-$ or any other pharmaceutically-acceptable organic or inorganic counterion.

It is recognised that certain compounds of general formula (I) may exist in two enantiomeric forms due to the chirality of the cobalt atom, and that certain compounds of general formula (II) may exist in various diastereomeric forms due to the chirality of both the nitrogen and cobalt atoms: in such cases, it is to be understood that general formulae (I) and (II) represent all such possible configurations and enantiomers.

In a second aspect, the invention relates to the class of cobalt complexes represented by the general formula (III)

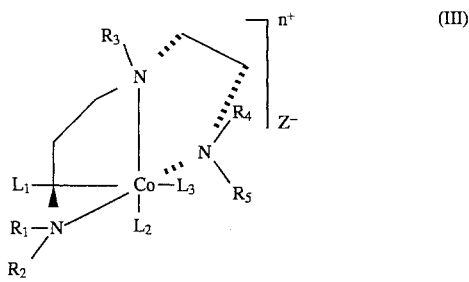

(III)

where $R_1$–$R_5$ separately represent H, lower alkyl (optionally substituted with hydroxy and/or amino functions) containing from 1 to 6 carbon atoms, or $CH_2CH_2Cl$, except that not more than two of $R_1$–$R_5$ shall represent $CH_2CH_2Cl$ groups in any one molecule; $L_1$–$L_3$ separately represent all possible combinations of $Cl^-$, $NO_2^-$ and $NH_3$ monodentate ligands, or a combination of one of these monodentate ligands together with a bidentate ligand (e.g., acetylacetonato), or may collectively represent a tridentate ligand, for example iminodiacetato, N-(Q)iminodiacetato where Q is lower alkyl (optionally substituted with hydroxy and/or amino functions) containing from 1 to 6 carbon atoms, glycylglycinato or 2,6-pyridinedicarboxylato; n is 0 or 1, and, when n=1, $Z^-$ represents $Cl^-$, $Br^-$, $I^-$, $ClO_4^-$, $NO_3^-$, $HCO_3^-$ or any other pharmaceutically-acceptable organic or inorganic counterion.

It is recognised that certain compounds of general formula (III) may exist in various isomeric forms: in such cases, it is to be understood that general formula (III) represents all such possible isomeric forms.

In a third aspect, the invention relates to the class of cobalt complexes represented by the general formulae (IV) and (V)

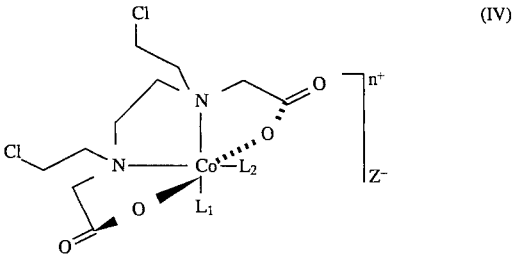

(IV)

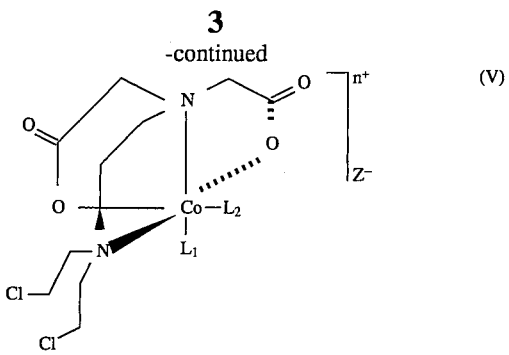

where $L_1$ and $L_2$ together represent two monodentate ligands (e.g., aquo or $NH_3$), or a bidentate ligand, for example ethylenediamine, 1,2-diaminopropane, 1,3-diaminopropane, 2,2'-bipyridine, o-phenanthroline, or N-(Q)amminoacetato where Q is lower alkyl (optionally substituted with hydroxy and/or amino functions) containing from 1 to 6 carbon atoms; n is 0 or 1, and, when n=1, $Z^-$ represents $Cl^-$, $Br^-$, $I^-$, $ClO_4^-$, $NO_3^-$, $HCO_3^-$ or any other pharmaceutically-acceptable organic or inorganic counterion.

It is recognised that certain compounds of general formulae (IV) and (V) may exist in various geometric, enantiomeric and diastereomeric forms around the nitrogen and cobalt atoms: in such cases, it is to be understood that general formulae (IV) and (V) represent all such possible configurations and enantiomers.

The compounds of formulae (I) to (V) have cytotoxic and antitumour activity, and are useful as antitumour agents.

The compounds of formulae (I) to (V) which contain amino functions can form pharmaceutically-acceptable addition salts with both organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, isethionic and the like.

The compounds of formulae (I) and (II) may be prepared by the process outlined in Scheme 1, which comprises deprotonation of the appropriate 3-R-2,4-pentanedionato ligands (prepared by the method of Johnson, Markham and Price. Organic Syntheses, Coll. Vol. V, p. 785) with aqueous NaOH, and reaction with the sodium salt of the hexanitrocobaltate complex, $Na_3[Co(NO_2)_6]$, to form bis-3-R-pentane-2,4-dionato dinitro cobalt (III) anion complexes, which were isolated as their sodium salts. A solution of the sodium salt of the appropriate cobalt acetylacetone complexes in a suitable solvent (preferably methanol/water mixtures) was then treated with a solution of the appropriate, freshly-deprotonated mustard ligand N,N-bis(2-chloroethyl)ethylenediamine (DCE) or N,N'-bis(2-chloroethyl)ethylenediamine (BCE) in a suitable solvent (preferably methanol/water mixtures), with or without the addition of activated charcoal, and stirring at a temperature between 0°–40° C. (preferably 20° C.) for the appropriate period, followed by addition of a suitable anion (preferably $NaClO_4$) to precipitate the complex of formulae (I) or (II). If desired, the $ClO_4^-$ salt can be changed by suspending the finely ground $ClO_4$ complex in water with 10–20% MeOH and stirring this with a 5-fold excess of Amberlite IRA-401 anion exchange resin (in a desired counterion form). After 1 h the suspension is filtered through a bed of the same anion exchange resin, and the filtrate concentrated to give the complex containing the desired counterion.

The mustard ligands BCE and DCE can be prepared by the process outlined in Scheme 2, or by similar methods.

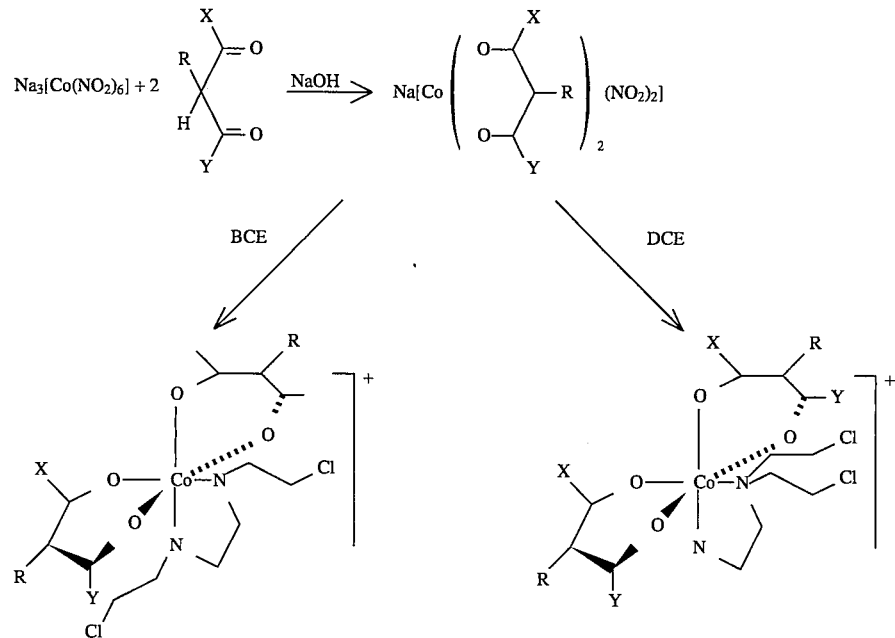

Scheme 1

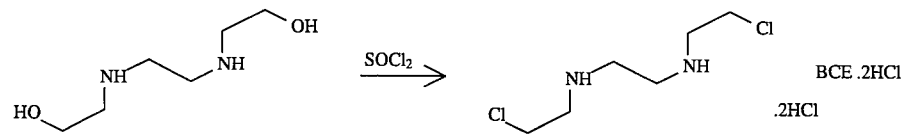

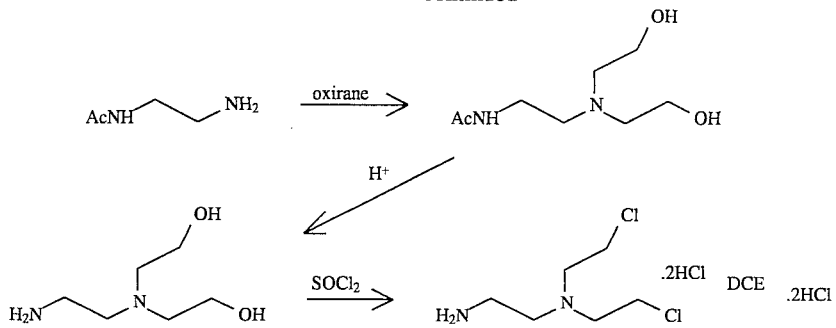

The compounds of formula (III) may be prepared by a process which comprises mixing a solution of the sodium salt of the hexanitrocobaltate complex, $Na_3[Co(No_2)_6]$, in a suitable solvent (preferably methanol/water mixtures) with a solution of the appropriate, freshly-deprotonated mustard ligand (eg, N'N'-bis(2-chloroethyl)diethylene triamine, DCD) in a suitable solvent (preferably methanol/water mixtures), with or without the addition of activated charcoal, and stirring at a temperature between 0°–40° C. (preferably 20° C.) for the appropriate period. Coordination of auxiliary non-mustard ligands may be accomplished by substituting one or more of the remaining nitro groups with the deprotonated form of the acid ligand (eg., 2,6-pyridinedicarboxylate dianion).

The mustard ligands (eg., DCD) can be prepared by the process outlined in Scheme 3, or by similar methods.

one carbonato group, with the basic form of the ligand (eg., ethylenediamine).

The mustard ligands can be prepared by the process outlined in Scheme 4, or by similar methods.

Scheme 4

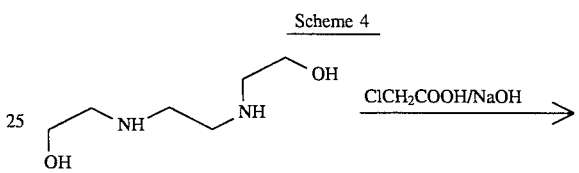

Scheme 3

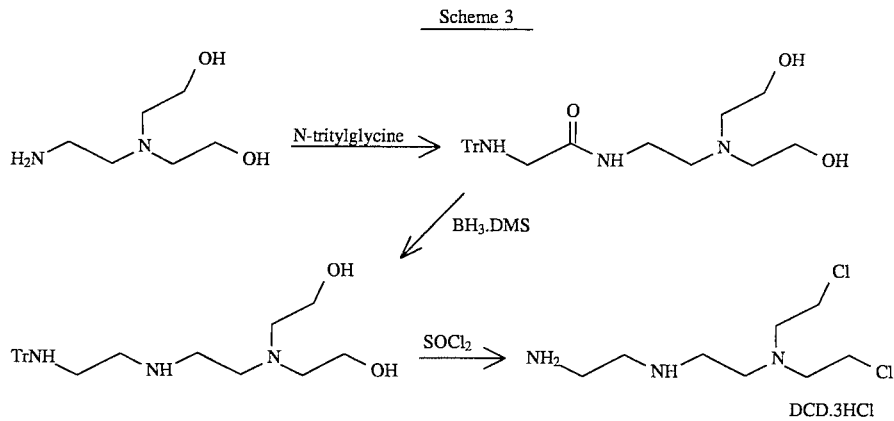

The compounds of formulae (IV) and (V) may be prepared by a process which comprises mixing a solution of an appropriate cobalt complex $Na_3[Co(NO_2)_6]$, $Na_3[Co(CO_3)_3]$ .$3H_2O$ or $K_3[Co(CO_3)_3]$.$3H_2O$ in a suitable solvent (preferably methanol/water mixtures) with a solution of the appropriate, freshly-deprotonated mustard ligand N,N'-bis-(2-chloroethyl)ethylenediamine-N',N-diacetic acid (BCEDA) or N,N-bis(2-chloroethyl)ethylenediamine-N',N'-diacetic acid (DCEDA) in a suitable solvent (preferably methanol/water mixtures), with or without the addition of activated charcoal, and stirring at a temperature between 0°–40° C. (preferably 20° C.) for the appropriate period. Alternatively, a solution of the freshly-deprotonated mustard ligand in a suitable solvent (preferably methanol/water mixtures) can be treated with $Co(II)(H_2O)_6^{2+}$, followed by $H_2O_2$. Coordination of auxiliary non-mustard bidentate ligands may be accomplished by substituting two nitro or aquo groups, or -continued
Scheme 4

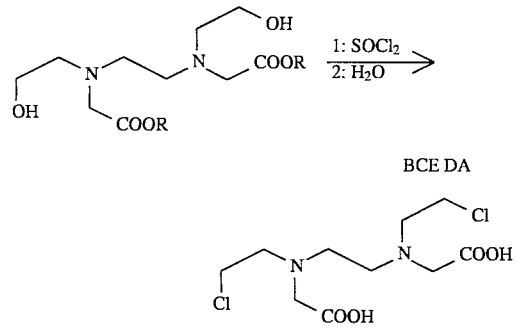

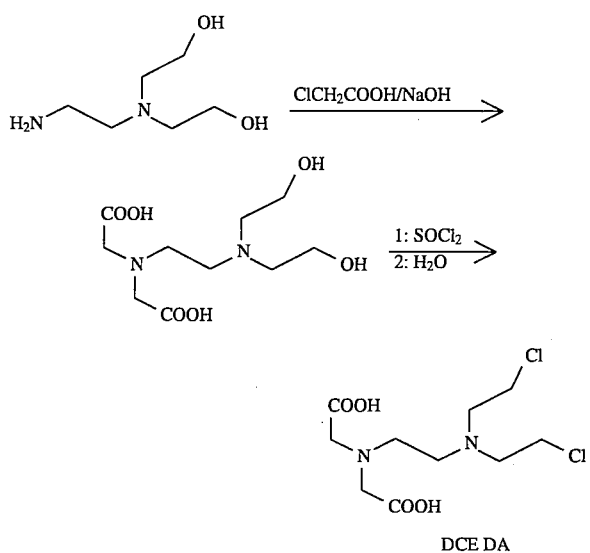

DCEDA

The following Table 1 sets out physical data for 10 compounds within the general formulae (I)–(V), representative of them, and preparable by the processes of the invention.

dissolve the solids gave N,N'-bis(2-chloroethyl)ethylenediamine dihydrochloride (BCE.2HCl).

[Co(acac)$_2$(BCE)]ClO$_4$ (1) by Method A Na[Co(acac)$_2$(NO$_2$)$_2$].H$_2$O (0.40 g, 1.025 mmol) was dissolved with stirring in a mixture of H$_2$O (6 mL) and MeOH (2 mL). To an ice-cooled solution of BCE.2HCl (0.279 g, 1.081 mmol) dissolved in H$_2$O (2 mL) was added 2.0 mL of a solution of NaOH (0.43 g) in MeOH (10 mL). Immediately, activated charcoal (0.25 g) was added to the solution containing the cobalt complex with stirring, followed rapidly by the solution of deprotonated BCE. The mixture was stirred for 20 min then filtered through Celite and the charcoal was washed once with water and once with MeOH. The washings were added to the filtrate, followed by NaClO$_4$.H$_2$O (3.2 g) in H$_2$O (3 mL), and the mixture was cooled in an ice bath. After 2 h the purple crystalline mass was filtered and washed twice with cold H$_2$O and three times with Et$_2$O and dried in air to give [Co(acac)$_2$(BCE)]ClO$_4$ (1) (0.475 g, 81.2%). $^1$H NMR (400 MHz, CD$_3$SOCD$_3$): δ 5.97 (br, 2H, NH), 5.66 (s, 2H, CH), 4.03, 3.93 (m, 2H, CH$_2$Cl); 2.86, 2.75 (m, 2H, CH$_2$NHR); 2.71, 2.58 (m, 2H, CH$_2$CH$_2$Cl), 2.14, 2.08 (s, 3H, CH$_3$CO). $^{13}$C NMR (100 MHz, CD$_3$SOCD$_3$): δ 189.47, 189.31 (CO); 97.93 (CH), 50.72 (CH$_2$Cl), 49.70 (CH$_2$NHR), 39.60 (CH$_2$CH$_2$Cl), 26.38, 26.25 (CH$_3$CO). Analysis. Calcd for C$_{16}$H$_{28}$N$_2$O$_8$Cl$_3$Co: C, 35.5; H, 5.2; N, 5.2; Cl, 19.6. Found: C, 35.3; H, 5.2; N, 5.1; Cl, 19.7.

TABLE 1

| | Compound | Preparative Method | Formula | Analysis | | | |
|---|---|---|---|---|---|---|---|
| | | | | C | H | N | Cl |
| 1 | [Co(acac)$_2$(BCE)]ClO$_4$ | A | C$_{16}$H$_{28}$Cl$_2$N$_2$O$_4$Co.ClO$_4$ | Calcd. 35.48 | 5.21 | 5.17 | 19.64 |
| | | | | Found 35.29 | 5.19 | 5.14 | 19.68 |
| 2 | [Co(Macac)$_2$(BCE)]ClO$_4$ | A | C$_{18}$H$_{32}$Cl$_2$N$_2$O$_4$Co.ClO$_4$ | Calcd. 37.95 | 5.66 | 4.92 | |
| | | | | Found 37.58 | 5.47 | 4.96 | |
| 3 | [Co(Etacac)$_2$(BCE)]ClO$_4$ | A | C$_{20}$H$_{36}$Cl$_2$N$_2$O$_4$Co.ClO$_4$ | Calcd. 40.18 | 6.07 | 4.69 | 17.79 |
| | | | | Found 40.24 | 6.02 | 4.82 | 18.06 |
| 4 | [Co(Pracac)$_2$(BCE)]ClO$_4$ | D | C$_{22}$H$_{40}$Cl$_2$N$_2$O$_4$Co.ClO$_4$ | Calcd. 42.21 | 6.44 | 4.48 | |
| | | | | Found 42.23 | 6.44 | 4.63 | |
| 5 | [Co(Clacac)$_2$(BCE)]Cl | B | C$_{16}$H$_{26}$Cl$_4$N$_2$O$_4$Co.Cl | Calcd. 35.15 | 4.79 | 5.13 | |
| | | | | Found 34.76 | 4.61 | 5.10 | |
| 6 | [Co(acac)$_2$(DCE)]ClO$_4$ | C, E | C$_{16}$H$_{28}$Cl$_2$N$_2$O$_4$Co.ClO$_4$ | Calcd. 35.48 | 5.21 | 5.17 | |
| | | | | Found 35.82 | 5.17 | 5.07 | |
| 7 | [Co(Macac)$_2$(DCE)]ClO$_4$ | E | C$_{18}$H$_{32}$Cl$_2$N$_2$O$_4$Co.ClO$_4$ | Calcd. 37.95 | 5.66 | 4.92 | 18.67 |
| | | | | Found 38.23 | 5.70 | 4.90 | 18.76 |
| 8 | [Co(Etacac)$_2$(DCE)]Cl.2H$_2$O | D | C$_{20}$H$_{40}$Cl$_2$N$_2$O$_4$Co.Cl.2H$_2$O | Calcd. 42.16 | 7.08 | 4.92 | 18.85 |
| | | | | Found 41.45 | 7.03 | 4.81 | 19.64 |
| 9 | mer-[Co(DCD)(NO$_2$)$_3$] | | C$_8$H$_{19}$Cl$_2$N$_6$O$_6$Co | correct $^1$H and $^{13}$C NMR | | | |
| 10 | [Co(DCEDA)(H$_2$O)$_2$]ClO$_4$ | | C$_{10}$H$_{16}$Cl$_2$N$_2$O$_6$Co.ClO$_4$ | correct UV/vis spectrum | | | |

The following Examples A–F illustrate the preparation of compounds representative of the general formulae (I) to (V)

EXAMPLE A

Preparation of Compound 1 ([Co(acac)$_2$(BCE)]ClO$_4$) of Table 1 by Method A and the Process of Schemes 1 & 2

N,N'-Bis(2-chloroethyl)ethylenediamine (BCE) A solution of N,N'-bis(2-hydroxyethyl)ethylenediamine (5.4 g, 0.036 mol) in SOCl$_2$ (60 mL) was heated at 90° C. for 2 h, then stirred at room temperature for 24 h. Excess SOCl$_2$ was then removed under reduced pressure, and the residue was triturated with isopropanol. Crystallisation from boiling isopropanol (800 mL) containing just enough water to Similar methods were used to make compounds 2 & 3 of Table 1, as follows:

[Co(Macac)$_2$(BCE)]ClO$_4$ (2) Na$_3$[Co(NO$_2$)$_6$] (3.27 g, 8.11 mmol) was dissolved in H$_2$O (11 mL) and added to a mixture of NaOH (0.70 g, 17.5 mmol) and 3-methylacetylacetone (2.0 g, 17.5 mmol) in H$_2$O (11 mL) which had been cooled in an ice bath. Rapid formation of red-brown crystals occurred after 10 min, and after cooling at 5° C. for 12 h these were collected by filtration and washed with Me$_2$CO, Et$_2$O and dried in air to give 2.81 g of crude product. This was recrystallized (1 g) by dissolving in H$_2$O (35 Ml) and filtering into NaNO$_2$ solution (5 g in 15 mL H$_2$O). The solution was filtered and the crystalline product was washed with EtOH/Me$_2$CO (2:1) and dried in air to give Na[Co(Macac)$_2$(NO$_2$)$_2$].H$_2$O (0.4 g, 12%). Analysis. Calcd. for C$_{12}$H$_2$OH$_2$O$_9$NaCo: C, 34.5; H, 4.8; N, 6.7. Found: C, 34.9; H, 4.3; N, 7.4%. Treatment of this as above gave

[Co(Macac)$_2$(BCE)]ClO$_4$ (2). $^{13}$C NMR (100 MHz, CDCl$_3$): major isomer δ 188.65, 188.20 (CO); 102.25 (CMe); 50.70 (CH$_2$Cl); 49.70 (CH$_2$NHR); 40.07 (CH$_2$CH$_2$Cl); 26.65, 26.33 (CH$_3$CO) and 14.95 (CH$_3$). Analysis. Calcd. for C$_{18}$H$_{32}$N$_2$O$_8$Cl$_3$Co: C, 37.9; H, 5.7; N, 4.9. Found: C, 37.6; H, 5.5; N, 5.0%.

[Co(Etacac)$_2$(BCE)]ClO$_4$ (3) A similar preparation via Na[Co(Etacac)$_2$(NO$_2$)$_2$] (uncharacterised) gave [Co(Etacac)$_2$(BCE)]ClO$_4$ (3). $^1$H NMR (400 MHz, CDCl$_3$): δ 4.88 (br s, 2H, NH); 3.89, 3.78 (m, 2H, CH$_2$Cl); 3.08 (br q, 2H, CH$_2$NHR); 2.76 (t, 2H, CH$_2$NHR); 2.40, 2.19 (m, 2H, CH$_2$ CH$_2$Cl); 2.35, 2.17 (s, 3H, CH$_3$CO); 2.32 (q, 4H, J=7.4 Hz, CH$_2$CH$_3$), 1.02 (t, 6H, J=7.4 Hz CH$_3$CH$_2$). $^{13}$C NMR (100 MHz, CDCl$_3$): δ 189.26, 189.13 (CO); 110.49 (CEt); 50.91 (CH$_2$Cl); 49.82 (CH$_2$NHR); 39.69 (CH$_2$CH$_2$Cl); 25.56, 25.00 (CH$_3$CO); 22.37 (CH$_2$CH$_3$), 15.17 (CH$_3$CH$_2$). Analysis. Calcd. for C$_{20}$H$_{36}$ N$_2$O$_8$Cl$_3$Co: C, 40.2; H, 6.1; N, 4.7; Cl, 17.8. Found: C, 40.2; H, 6.0; N, 4.8, Cl, 18.1%.

EXAMPLE B

Preparation of Compound 5
([Co(Clacac)$_2$(BCE)]Cl) of Table 1 by Method B

N-Chlorosuccinimide (0.204 g, 1.53 mmol) was dissolved in MeOH (60 mL). [Co(acac)$_2$(BCE)]ClO$_4$ (0.24 g, 0.443 mmol) was added portion-wise and the solution was stirred for 6 h at 20° C. The solvent volume was reduced to 30 mL and H$_2$O (50 mL) was added. The solution was loaded onto a Sephadex-SP-C25 cation exchange column (2.5×10 cm) prepared in the Na$^+$ form. The column was washed with water and the complex was eluted with 0.1 mol L$^{-1}$ NaCl, leaving a yellow brown band on the column. The eluted band was extracted five times with CH$_2$Cl$_2$ and the combined extracts were evaporated. Toluene (5 mL) was added to the residue, and the solution was further evaporated to give a magenta coloured oil. Addition of Me$_2$CO (3 mL) produced a mass of fine needles of [Co(Clacac)$_2$(BCE)]Cl (5) (0.158, 55.5%), which were filtered and washed quickly with Me$_2$CO followed by Et$_2$O, and dried in air in a desiccator. $^1$H NMR (400 MHz, CDCl$_3$): δ 5.86 (br, 2H, NH); 3.97 (m, 4H, CH$_2$Cl); 3.00 (m, 4H, CH$_2$NHR); 2.95 (m, 4H, C H$_2$CH$_2$Cl) and 2.49, 2.42 (s, 3H, CH$_3$CO). $^{13}$C NMR (100 MHz, CDCl$_3$): δ 188.74, 188.45 (CO); 107.06 (CCl); 51.10 (CH$_2$Cl); 50.16 (CH$_2$NHR); 39.92 (CH$_2$ CH$_2$Cl) and 28.26, 27.60 (CH$_3$CO) Analysis. Calcd. for C$_{16}$H$_{26}$N$_2$O$_4$Cl$_5$Co: C, 35.2; H, 4.8; N, 5.1. Found: C, 34.8; H, 4.6; N; 5.1%.

EXAMPLE C

Preparation of Compound 6
([Co(acac)$_2$DCE)]ClO$_4$) of Table 1 by Method C
and the Process of Schemes 1 and 2

N,N-Bis(2-hydroxyethyl)ethylenediamine Oxirane (27.0 g, 0.60 mol) was added to a cooled (5° C.) solution of N-acetylethylenediamine (25.0 g, 0.24 mol) in water (50 mL). The solution was stirred for 4 h at 5° C. and then overnight at room temperature before being concentrated under reduced pressure. The residue was chromatographed on SiO$_2$, and elution with EtOAc/MeOH (9:1) gave N-acetyl-N',N'-bis(2-hydroxyethyl)ethylenediamine as a viscous oil (35.7 g, 78%). This was used directly, the entire sample being dissolved in conc. HCl (250 mL) and warmed to 90° C. for 20 h, then concentrated under reduced pressure to give the dihydrochloride salt of N,N-bis-(2-hydroxyethyl)ethylenediamine as a syrup. This was dissolved in MeOH, and the solution was neutralised with powdered KHCO$_3$, filtered and evaporated. The residue was triturated with Me$_2$CO/MeOH (1:1), and the triturate was evaporated to give N,N-bis(2-hydroxyethyl)ethylenediamine as a straw-coloured liquid, which was used without further characterization.

N,N-Bis(2-chloroethyl)ethylenediamine (DCE) A solution of the above diol (2.96 g, 0.02 mol) in SOCl$_2$ (150 mL) was stirred at room temperature for 48 h. Excess SOCl$_2$ was then removed under reduced pressure, and the residue was dissolved in water and washed several times with EtOAc. The aqueous layer was evaporated to dryness under reduced pressure, and the resulting crude residue was crystallised from MeOH to give N,N-bis-(2-chloroethyl)ethylenediamine dihydrochloride (DCE.2HCl) as hygroscopic white plates, mp 136° C. (Price, Kavas and Nakata, *J. Med. Chem.*, 1965, 8, 650, record mp 139°–140° C.).

[Co(acac)$_2$(DCE)]ClO$_4$) (6) by Method C (DCE.2HCl) (0.364 g, 1.41 mmol) was suspended in MeOH (5 mL) and NaOH (0.113 g, 2.82 mmol) in MeOH (2 mL) was added. The solution was immediately added to a solution of Co(acac)$_3$ (0.457 g, 1.28 mmol) in MeOH (45 mL) followed by activated charcoal (0.1 g). The solution was stirred for 1 h then filtered through Celite. The combined green-red filtrate and washings were evaporated to small volume under reduced pressure and H$_2$O (50 mL) was added. Green crystals of unreacted Co(acac)$_3$ which formed were filtered off and the filtrate was then loaded on to a Sephadex-SP-C25 column (60 mL) in the Na$^+$ form. The column was washed with water, the elution was begun with 0.05 mol L$^{-1}$ NaCl and finished with 0.1 mol L$^{-1}$ NaCl. The eluted band was extracted with CHCl$_3$ four times and the combined extracts were evaporated to dryness under reduced pressure. The residue was taken up in water and NaClO$_4$.H$_2$O (1 g) in MeOH was added. After cooling at 5° C. for 2 days the dark crystals of [Co(acac)$_2$(DCE)]ClO$_4$ (6) which had formed (0.03 g, 4.3%) were filtered and washed with H$_2$O and dried in air in a desiccator. $^1$H NMR (400 MHz, CDCl$_3$): δ 5.60, 5.53 (s, 1H, CH); 4.39, 4.22 (br m, 1H, NH$_2$); 3.93, 3.69, 3.59, 3.50 (m, 1H, CH$_2$Cl); 3.07 (m, 2H, CH$_2$NH$_2$); 2.79 (t, 2H, J=6.3 Hz, CH$_2$NR$_2$); 3.02, 2.61, 2.38, 2.26 (m, 1H, C H$_2$CH$_2$Cl) and 2.21, 2.19, 2.10, 1.97 (s, 3H, CH$_3$CO). $^{13}$C NMR (100 MHz, CDCl$_3$): δ 191.51, 191.46, 191.12, 189.91 (CO); 99.81, 98.46 (CH); 61.40 (CH$_2$NR$_2$); 55.71, 53.77 (CH$_2$Cl); 42.11 (CH$_2$NH$_2$); 37.97, 35.97 (CH$_2$CH$_2$Cl) and 26.68, 26.64, 26.26, 25.71 (CH$_3$O). Analysis. Calcd. for C$_{16}$H$_{28}$N$_2$O$_8$Cl$_3$Co: C, 35.5; H, 5.2; N, 5.2. Found: C,, 35.8; H, 5.1; N, 5.1%.

EXAMPLE D

Preparation of Compound 8
([Co(Etacac)$_2$(DCE)]Cl.2H$_2$O) of Table 1 by
Method D and the Process of Scheme 1

DCE.2HCl (0.856 g, 3.319 mmol) was dissolved in H$_2$O (2 mL) and NaOH (0.265 g, 6.638 mmol) dissolved in a mixture of H$_2$O (1 mL) and MeOH (5 mL) was added. Immediately this solution was added to a solution of Na[Co(Etacac)$_2$(NO$_2$)$_2$].H$_2$O (1.288 g, 2.886 mmol) in H$_2$O (10 mL) and MeOH (20 mL) to which activated charcoal (0.28 g) had been added. The mixture was stirred for 1 h then filtered through Celite and the charcoal washed with water and MeOH which were added to the filtrate. HCl (3 mol L$^{-1}$) was added to the filtrate until the solution was acidic and it was then extracted three times with CHCl$_3$. The combined extracts were evaporated under reduced pressure to a thick oil, which was dissolved in a mixture of MeOH (10 mL) and H$_2$O (10 mL), and extracted three times with CHCl$_3$ (10 mL). The combined extracts were once again evaporated to an oil and then taken up in MeOH (15 mL) and H$_2$O (15 mL) and loaded on to a Sephadex-SP-C25 cation exchange resin (Na$^+$ form) column and eluted with 0.15 mol L$^{-1}$ NaCl in 10% MeOH/H$_2$O. The green eluant was extracted five times with CHCl$_3$ and the combined extracts (50 mL total) were evaporated under reduced pressure to give an oil, which was dissolved in Et$_2$O and then evaporated to dryness to give [Co(Etacac)$_2$(DCE)]Cl.2H$_2$O (8) as a green solid (455 mg, 29.5%). $^1$H NMR (400 MHz, CDCl$_3$): δ 5.54, 4.46 (br, 1H, NH$_2$); 4.02, 3.76 (m, 1H, CH$_2$Cl); 3.53 (m, 2H, CH$_2$Cl); 3.43, 2.69, 2.61, 2.30 (m, 1H, C$\underline{H}_2$CH$_2$Cl); 3.17 (br s, C$\underline{H}_2$NH$_2$); 2.93 (br m, 2H, CH$_2$NR$_2$); 2.40, 2.35, 2.23, 2.09 (s, 3H, CH$_3$CO); 2.37, 2.29 (q, 2H, J=7.4 Hz, C$\underline{H}_2$CH$_3$) and 1.05 (t, 6H, J=7.4 Hz, CH$_3$C$\underline{H}_2$). $^{13}$C NMR (100 MHz, CDCl$_3$): δ 189.78, 189.09, 189.00, 188.21 (CO); 111.59, 109.32 ($\underline{C}$Et); 61.57 (CH$_2$NR$_2$); 55.43, 53.73 (CH$_2$Cl); 41.84 (CH$_2$NH$_2$); 37.65, 36.17 ($\underline{C}$H$_2$CH$_2$Cl); 25.82, 25.70, 25.30, 24.55 ($\underline{C}$H$_3$CO); 22.38, 22.32 ($\underline{C}$H$_2$CH$_3$) and 15.28, 14.79, ($\underline{C}$H$_3$CH$_2$). Analysis. Calcd for C$_{20}$H$_{40}$N$_2$O$_6$Cl$_3$Co: C, 42.2; H, 7.1; N, 4.9; Cl, 18.9. Found: C, 41.5; H, 7.0; N, 4.8; Cl, 19.6%.

Similar methods were used to make compound 4 of Table 1, as follows:

[Co(Pracac)$_2$(BCE)]ClO$_4$ (4) Na(Pracac) (0.50 g, 3.05 mmol) was dissolved in H$_2$O (2 mL). A solution of Na$_3$[Co(NO$_2$)$_6$] dissolved in H$_2$O (2 mL) was added. A small amount of gelatinous material was filtered off and MeOH (2 mL) was added to the filtrate. The solution was sealed and left to stand overnight then opened and the MeOH was allowed to slowly evaporate, giving red crystals of Na[Co(Pracac)$_2$(NO$_2$)$_2$].H$_2$O (0.115 g, 16%), which were filtered, washed with a small amount of H$_2$O and dried in air. Analysis. Calcd for C$_{16}$H$_{28}$N$_2$O$_9$NaCo: C, 40.5; H, 5.9; N, 5.9. Found: C, 40.6; H, 5.9; N, 6.0%.

Treatment of this as above gave [Co(Pracac)$_2$(BCE)]ClO$_4$ (4). $^1$H NMR (400 MHz, CDCl$_3$): δ 4.87 (br s, 2H, NH); 3.88, 3.77 (m, 2H, CH$_2$Cl); 3.08 (dd, 2H, J=7.8, 3.7 Hz, C$\underline{H}_2$NHR); 2.76 (dd, 2H, J=8.3, 11.0 Hz, C$\underline{H}_2$NHR); 2.39, 2.16 (m, 2H, C$\underline{H}_2$CH$_2$Cl); 2.34, 2.16 (s, 3H, C$\underline{H}_3$ CO); 2.26 (t, 4H, J=7.8 Hz, C$\underline{H}_2$CH$_2$CH$_3$); 1.38 (m, 4H, C$\underline{H}_2$CH$_3$) and 0.95 (t, 6H, J=7.3 Hz, CH$_3$). $^{13}$C NMR (100 MHz, CDCl$_3$): δ 189.39, 189.24 (CO); 109.00 ($\underline{C}$Pr); 50.89 (CH$_2$Cl); 49.8 (CH$_2$NHR); 39.67 ($\underline{C}$H$_2$CH$_2$Cl); 31.19 ($\underline{C}$H$_2$CH$_2$CH$_3$); 25.80, 25.28 ($\underline{C}$H$_3$CO); 24.21 ($\underline{C}$H$_2$CH$_3$) and 13.86 (CH$_3$). Analysis. Calcd. for C$_{22}$H$_{40}$N$_2$O$_8$Cl$_3$Co: C, 42.2; H, 6.4; N, 4.5. Found: C, 42.4; H, 6.4; N, 4.6%.

EXAMPLE E

Preparation of Compound 7 ([Co(MacaC)$_2$(DCE)]ClO$_4$) of Table 1 by Method E and the Process of Scheme 1

Na[Co(Macac)$_2$(NO$_2$)$_2$].H$_2$O (1.50 g, 3.587 mmol) was dissolved in a mixture of MeOH (46 mL) and H$_2$O (27 mL). A solution of NaOH (0.330 g, 8.248 mmol) dissolved in MeOH (8 mL) was added to a solution of DCE.HCl (1.064 g, 4.124 mmol) in H$_2$O (1 mL) which had been cooled in an ice bath. After 30 sec, activated charcoal (0.42 g) was added to the Na[Co(Macac)$_2$(NO$_2$)$_2$].H$_2$O solution, followed immediately by the deprotonated DCE solution and the mixture stirred for 1 h. The charcoal was filtered off through Celite and washed with MeOH, which was added to the filtrate. The filtrate was acidified with 3 mol L$^{-1}$ HCl (1.5 mL) and extracted with three portions of CHCl$_3$. The combined extracts were evaporated to dryness under reduced pressure, and the residue was taken up in H$_2$O (20 mL) and decanted from some insoluble material. MeOH (20 mL) was then added to the supernatant, and the solution was left open to the air at 20° C. for slow evaporation of the MeOH. After one week, the resulting green crystals of [Co(Macac)$_2$(DCE)]ClO$_4$ (7) (0.205 g, 10%) were collected by filtration and washed with 20% MeOH/H$_2$O, then with H$_2$O, and finally with Et$_2$O. The product was air dried in a desiccator. $^1$H NMR (400 MHz, CDCl$_3$): δ 4.30, 4.01 (br, 1H, NH$_2$); 4.07, 3.78, 3.60, 3.59 (m, 1H, CH$_2$Cl); 3.10 (m, 2H, C$\underline{H}_2$NH$_2$); 2.98, 2.76 (m, 1H, CH$_2$NR$_2$); 2.61, 2.50, 2.25 (m, 1H, C$\underline{H}_2$CH$_2$Cl); 2.35, 2.33 (s, 3H, CH$_3$) and 2.24, 2.09, 1.98, 1.90 (s, 3H, CH$_3$CO). $^{13}$C NMR (100 MHz, CDCl$_3$): δ 189.42, 189.20, 188.87, 187.71 (CO); 103.83, 102.16 ($\underline{C}$Me); 61.15 ($\underline{C}$H$_2$NR$_2$); 55.67, 53.60 (CH$_2$Cl); 41.83 (CH$_2$NH$_2$); 38.17, 36.03 ($\underline{C}$H$_2$CH$_2$Cl); 26.46, 26.38, 26.24, 25.64 ($\underline{C}$H$_3$CO) and 14.89, 14.69, (CH$_3$). Analysis. Calcd for C$_{18}$H$_{32}$N$_2$O$_8$Cl$_3$Co: C, 38.0; H, 5.7; N, 4.9; Cl, 18.7. Found: C, 38.2; H, 5.7; N, 4.9; Cl, 18.8%.

EXAMPLE F

Preparation of Compound 9 (mer-[Co(DCD)(NO$_2$)$_3$]) of Table 1 by the Method of Scheme 3

N-{[N',N'-bis(2-hydroxyethyl)]-2-aminoethyl}-N"-tritylglycyl carboxamide 1,1'-Carbonyldiimidazole (26.0 g, 0.16 mol) was added to a solution of N-tritylglycine (40.0 g, 0.13 mol) in dry DMF (200 mL). After CO$_2$ evolution ceased, the solution was warmed to 40° C. for 10 min, and a solution of the N,N-bis(2-hydroxyethyl)ethylenediamine (see Example A) in DMF (50 mL) was added in one portion. After 30 min, solvent was evaporated under reduced pressure, and the residue was partitioned between EtOAc and saturated NaHCO$_3$. The organic layer was washed well with brine, and worked up to give an oil which was chromatographed on SiO$_2$. EtOAc eluted unidentified material, while EtOAc/MeOH (19:1) gave N-{[N',N'-bis(2-hydroxyethyl)]-2-aminoethyl}-N"-tritylglycyl carboxamide as a viscous oil (41.9 g, 72%). $^1$H NMR (CDCl$_3$) δ 7.73 (t, 1H, J=5.6 Hz, CONH), 7.39 (d, 6H, J=7.3 Hz, ArH), 7.25 (t, 6H, J=7.3 Hz, ArH), 7.17 (t, 3H, J=7.3 Hz, ArH), 3.92 (br, 3H, OH & NH), 3.51 (t, 4H, J=5.0 Hz, NCH$_2$C$\underline{H}_2$OH), 3.33 (dr, 2H, J=5.8, 5.6 Hz, CONHC$\underline{H}_2$), 2.94 (s, 2H, TrNHC$\underline{H}_2$ CO), 2.60 (2×t, 6H, C$\underline{H}_2$N(C$\underline{H}_2$CH$_2$OH)$_2$. $^{13}$C NMR (CDCl$_3$) δ 172.54 (CONH), 145.30 (3C)(Ar-C), 128.52 (6C)(Ar-C), 128.03 (6C)(Ar-C), 126.66 (3C)(Ar-C), 70.91 ($\underline{C}$Ph$_3$), 59.62 (2C)(NCH$_2\underline{C}$H$_2$OH), 56.89 (2C)(N$\underline{C}$H$_2$CH$_2$ OH), 54.84 (TrNH$\underline{C}$H$_2$CO), 48.07 (NCH$_2$), 37.67 (NCH$_2$).

The identity of this compound was further established by detritylation. A solution (10.0 g, 0.022 mol) in MeOH (100 mL) was treated with conc. HCl (40 mL), and the mixture was warmed at 50° C. for 30 min then concentrated to dryness under reduced pressure. The residue was dissolved in water, and the aqueous layer was washed well with EtOAc and then concentrated to dryness under reduced pressure to give the dihydrochloride salt of N-{[N',N'-bis(2-hydroxyethyl)]-2-aminoethyl}glycyl carboxamide (5.8 g, 95%). Crystallization from MeOH/Et$_2$O gave glistening plates, mp 158°–160° C. $^1$H NMR (D$_2$O) δ 3.96 (t, 4H, J=5.0 Hz, C$\underline{H}_2$OH), 3.86 (s, 2H, H$_3$N$^+$ C$\underline{H}_2$CO), 3.72 (t, 2H, J=6.2 Hz, CONHC$\underline{H}_2$), 3.53 (t, 2H, J=6.2 Hz, CH$_2$N$^+$), 3.48 (br t, 4H, J=5.0 Hz, N$^+$C$\underline{H}_2$CH$_2$OH). $^{13}$C NMR (D$_2$O) δ 170.89 (CONH), 58.08 & 57.80 (both 2C)(N$^+\underline{C}$H$_2$CH$_2$OH), 55.76

($H_3N^+$ $\underline{C}H_2CO$), 43.12 (CON$\underline{H}CH_2$), 37.20 ($CH_2N^+$). Anal. Calcd for $C_8H_{19}N_3O_3 \cdot 2HCl$: C, 34.5; H, 7.6; N, 15.1; Cl, 25.5. Found: C, 34.5; H, 7.6; N, 15.1; Cl, 25.6%.

$N^1,N^1$-Bis(2-hydroxyethyl)-$N^3$-trityldiethylenetriamine A solution of the carboxamide (10.0 g, 0.022 mol) in THF (200 mL) was treated dropwise at 0° C. under $N_2$ with borane-methyl sulfide complex (6.81 mL of 10.5N, 0.071 mol). After gas evolution ceased, the solution was heated under reflux for 4 h, then cooled to 0° C. and the excess reagent was destroyed by the dropwise addition of MeOH. The mixture was partitioned between EtOAc and water, and the residue from the organic layer was chromatographed on $SiO_2$. EtOAc eluted unidentified material, while EtOAc/MeOH (19:1) gave $N^1,N^1$-bis(2-hydroxyethyl)-$N^3$-trityldiethylenetriamine (6.14 g, 64%), which crystallised from $Me_2CO$ as cubes, mp 154° C. $^1$H NMR ($CDCl_3$) δ 7.45 (br d, 6H, J=7.3 Hz, ArH), 7.25 (br t, 6H, J=7.3 Hz, ArH), 7.16 (br t, 3H, J=7.3 Hz, ArH), 4.44 (br, 4H, OH & NH), 3.52 (t, 4H, J=4.9 Hz, NCH$_2$C$\underline{H}_2$OH), 2.84 (t, 2H, J=5.8 Hz, NHC$\underline{H}_2$CH$_2$NR$_2$), 2.75 (br t, 2H, J=4.8 Hz, C$\underline{H}_2$ N), 2.66 (br t, 2H, J=4.8 Hz, C$\underline{H}_2$N), 2.55 (t, 4H, J=4.9 Hz, NC$\underline{H}_2$CH$_2$OH), 2.42 (t, 2H, J=5.8 Hz, C$\underline{H}_2$N). $^{13}$C NMR ($CDCl_3$) δ 145.7 (3C)(Ar-C), 128.67 (6C)(Ar-C), 128.86 (6C)(Ar-C), 126.37 (3C)(Ar-C), 71.01 ($\underline{C}Ph_3$), 59.50 (2C)(NCH$_2$$\underline{C}H_2$OH), 57.31 (2C)(N$\underline{C}H_2$CH$_2$OH), 52.26 (NCH2), 49.08 (NCH$_2$), 46.58 (NCH$_2$), 41.43 (NCH$_2$).

$N^1,N^1$-Bis(2-chloroethyl)diethylenetriamine trihydrochloride A solution of the above N-trityltriamine (6.81 g, 0.016 mol) in $SOCl_2$ (200 ml) was stirred at room temperature for 48 h. Excess $SOCl_2$ was then removed under reduced pressure, and the residue was dissolved in water and washed several times with EtOAc. The aqueous layer was then evaporated to dryness under reduced pressure, and the residue was recrystallised several times from MeOH/Et$_2$O to give $N^1,N^1$-bis(2-chloroethyl)diethylenetriamine trihydrochloride (DCD.3HCl) as hygroscopic plates, mp 138°–140° C. (4.12 g, 86%). $^1$H NMR ($D_2O$) δ 4.03 (t, 4H, J=5.5 Hz, N$^+$CH$_2$C$\underline{H}_2$Cl), 3.79 (t, 4H, J=5.5 Hz, N$^+$C$\underline{H}_2$CH$_2$Cl), 3.77 (m, 2H, CH$_2$N$^+$), 3.71 (m, 2H, CH$_2$N$^+$), 3.57 (t, 2H, J=7.0 Hz, CH$_2$N$^+$), 3.46 (t, 2H, J=7.0 Hz, CH$_2$N$^+$H$_3$). $^{13}$C NMR ($D_2O$) δ 57.67 (2C)(N$^+$$\underline{C}H_2$CH$_2$Cl), 51.46 (CH$_2$N$^+$), 47.36 (CH$_2$N$^+$), 44.44 (CH$_2$N$^+$), 40.00 (2C)(N$^+$CH$_2$$\underline{C}H_2$Cl), 37.98 (CH$_2$N$^+$H$_3$). Anal. Calcd for $C_8H_{19}Cl_2N_3 \cdot 3HCl$: C, 28.5; H, 6.6; N, 12.5. Found: C, 28.2; H, 6.8; N, 12.2%.

mer-[Co(DCD)(NO$_2$)$_3$] (9) Na$_3$[Co(NO$_2$)$_6$] (0.415 g, 1.027 mmol) was dissolved in warm (35°–40° C.) H$_2$O (3 mL). DCD.3HCl (0.347 g, 1.028 mmol) was dissolved in H$_2$O (2 mL) and NaOH (0.123 g, 3.084 mmol) in 50% MeOH/H$_2$O (2 mL) was added with stirring. After 30 sec this solution was added to the Na$_3$[Co(NO$_2$)$_6$] solution with rapid stirring. Immediately an orange precipitate began to form. After 15 min more H$_2$O (4 mL) was added and the solution was stirred while cooling in an ice bath. The orange precipitate of mer-[Co(DCD)(NO$_2$)$_3$] (9) (0.298 g, 68%) was filtered and washed once with H$_2$O and five times with Et$_2$O, then dried in air in a desiccator. $^1$H NMR (CD$_3$SOCD$_3$) δ 5.69 (br d, 1H, NH), 5.35 (br s, 1H, NH), 5.15 (br s, 1H, NH), 3.68 (t, 4H, J=6.67 Hz, CH$_2$Cl), 2.88 (m, 8H, C$\underline{H}_2$CH$_2$Cl & C$\underline{H}_2$NHC$\underline{H}_2$), 2.63 (m, 2H, C$\underline{H}_2$N(CH$_2$CH$_2$Cl)$_2$), 2.30 (m, 2H, C$\underline{H}_2$NH$_2$). $^{13}$C NMR (CD$_3$SOCD$_3$) δ 54.88 ($\underline{C}H_2$N(CH$_2$CH$_2$Cl)$_2$), 50.39 (CH$_2$$\underline{C}H_2$Cl), 49.09 & 47.20 ($\underline{C}H_2$NH$\underline{C}H_2$), 42.91 ($\underline{C}H_2$NH$_2$), 41.95 ($\underline{C}H_2$ CH$_2$Cl).

EXAMPLE G

Preparation of Compound 10 of Table 1 by the Method of Scheme 4

A solution of chloroacetic acid (16.45 g, 0.17 moL) in water (100 mL) was cooled to 5° C. and treated dropwise with a solution of NaOH (13.93 g, 0.35 mol) in water (50 mL), keeping the temperature below 10° C. A solution of N,N-bis(2-hydroxyethyl)ethylenediamine (12.90 g, 0.087 mol) in water (70 mL) was added, and the solution was stirred at 20° C. for 30 min and warmed over 2 h to 50° C. After a further 1 h at this temperature, the solution was cooled, acidified with conc. HCl, and concentrated to dryness under reduced pressure. Crystallization of the residue from MeOH/Et$_2$O gave N,N-bis(2-hydroxyethyl)ethylenediamine-N',N'-diacetic acid dihydrochloride as a sticky solid (20.6 g, 70%). $^1$H NMR (D$_2$O) δ 4.02 (s, 4H, NC$\underline{H}_2$COOH), 3.99 (t, J=7 Hz, 4H, C$\underline{H}_2$OH), 3.60 (m, 8H, C$\underline{H}_2$N). [M. Ishidate, Y. Sakurai and K-I. Sawatari, Chem. Pharm. Bull., 9, 679–684 (1961) report mp 190°–191° C. for the free base].

The above salt was dissolved in MeOH (300 mL) and the solution was saturated with HCl gas and heated under gentle reflux for 15 h. Concentration under reduced pressure gave dimethyl N,N-bis(2-hydroxyethyl)ethylenediamine-N',N'-diacetate dihydrochloride as a sticky gum, which was used directly. $^1$H NMR (D$_2$O) δ 4.02 (m, 4H, CH$_2$OH), 3.85 (s, 4H, NC$\underline{H}_2$COOMe), 3.72 (s, 6H, 2×Me), 3.45 (m, 8H, NC$\underline{H}_2$).

The above diester (20.0 g) was dissolved in SOCl$_2$ (200 mL), kept at 20° C. for 48 h, then evaporated to dryness under reduced pressure to give dimethyl N,N-bis(2-chloroethyl)ethylenediamine-N',N'-diacetate dihydrochloride as a gum (20.6 g, 93%). $^1$H NMR (D$_2$O) δ 3.86 (s, 4H, NC$\underline{H}_2$COOMe), 3.84 (s, 6H, 2×Me), 3.77 (br s, 8H, NCH$_2$CH$_2$Cl), 3.37 (m, 4H, NCH$_2$CH$_2$N). A solution of this compound (20 g) in conc. HCl (200 mL) was warmed at 80° C. for 4 h. then evaporated to dryness under reduced pressure. The residue was dried over P$_2$O$_5$ under high vacuum for 24 h, then crystallized from MeOH/Et$_2$O, to give N,N-bis(2-chloroethyl)ethylenediamine-N',N'-diacetic acid dihydrochloride (DCEDA.2HCl) as a hygroscopic powder (15.1 g, 81%). $^1$H NMR (D$_2$O) δ 3.82 (s, 4H, NC$\underline{H}_2$COOH), 3.74 (br s, 8H, NCH$_2$CH$_2$Cl), 3.30 (m, 4H, NCH$_2$CH$_2$N).

The isomeric N,N'-bis(2-chloroethyl)ethylenediamine-N',N-diacetic acid dihydrochloride (BCEDA.2HCl) was prepared similarly from N,N'-bis(2-hydroxyethyl)ethylenediamine. Treatment of this with chloroacetic acid as above gave the corresponding N,N'-diacetic acid, which was esterified with methanolic HCl, chlorinated with SOCl$_2$, and hydrolysed with conc. HCl as described above for the isomeric compound to give BCEDA.2HCl, mp (MeOH/EtOAc) 190°–200° C. [M. Ishidate, Y. Sakurai and K-I. Sawatari, Chem. Pharm. Bull., 9, 679–684 (1961) report mp 187° C.]. $^1$H NMR (D$_2$O) δ 3.86 (s, 4H, NC$\underline{H}_2$COOH), 3.65 (br s, 8H, NCH$_2$CH$_2$Cl), 3.30 (m, 4H, NCH$_2$CH$_2$N).

Freshly-prepared Na$_3$[Co(CO$_3$)$_3$].3H$_2$O (0.44 g, 1.22 mmol) was suspended in H$_2$O (4 mL) and DCEDA.2HCl (0.5 g, 1.34 mmol) was added all at once with stirring. The solution was warmed at 40° C. for 10 min, after which time effervescence had ceased, and the violet colour of the solution indicated formation of the Co complex. Excess aqueous HClO$_4$ was added, and the resulting red-violet solution was cooled to 0° C. and diluted with EtOH followed by Et$_2$O to give crude [Co(DCEDA)(H$_2$O)$_2$].ClO$_4$ as a solid (0.3 g).

The following Table 2 gives biological data for selected examples of the compounds listed in Table 1. The abbreviations used in Table 2 are:

No. The number given the corresponding compound in Table 1.

IC$_{50}$ Growth inhibition studies were performed as described in detail elsewhere (W. R. Wilson, R. F. Anderson and W. A. Denny. J. Med. Chem., 1989, 32, 23; G. J. Finlay, B. C. Baguley and W. R. Wilson. Anal. Biochem., 1984, 139, 172.), using 200 viable AA8 or 300 viable UV4 cells plus 5000 lethally-irradiated AA8 feeder cells per well in 96-well tissue culture dishes. AA8 and UV4 cells were maintained in logarithmic-phase growth in 25 cm$^3$ tissue culture flasks with subculture twice weekly by trypsinization. The growth medium was antibiotic-free Alpha MEM with 10% v/v heat-inactivated (56° C., 40 min) fetal calf serum. Doubling times were approximately 14 h for AA8 and 15 h for UV4 cells. Cultures were tested for mycoplasma contamination frequently, using a cytochemical staining method.(I. R. Chen, Exp. Cell Res., 1977, 104, 255. Drugs were added 24 hours after initiating cultures in 96-well dishes, and cells were incubated under aerobic or hypoxic conditions for 18 hours before washing with fresh medium. The IC$_{50}$ was determined as the drug concentration needed to reduce the cell mass (protein content, measured after 72–78 h by staining with methylene blue and measuring absorbance in a microplate photometer) to 50% of the mean value for 8 control cultures on the same 96-well plate, air/N$_2$ ratio Ratio of IC$_{50}$ values after exposure as detailed above under either aerobic (air) or hypoxic (N$_2$) conditions (=aerobic IC$_{50}$/hypoxic IC$_{50}$).

HF Ratio of IC$_{50}$ values for a compound after exposure as detailed above against AA8 and UV4 cell lines (=IC$_{50}$(AA8)/IC$_{50}$(UV4)).

E½ Peak potentials (vs NHE) of cathodic wave, determined by square wave voltammetry at a platinum disc electrode in 0.15M (n-Bu$_4$N)ClO$_4$ in CH$_2$Cl$_2$ with ferrocene as an internal reference.

TABLE 2

Biological data for selected Co(III) complexes of Table 1

| No. | E$_{1/2}$ (mV) | IC$_{50}$ (air) AA8 | IC$_{50}$ (air)/IC$_{50}$ (N$_2$) AA8 | UV4 | HF (air) |
|---|---|---|---|---|---|
| 1 | −308 | 893 ± 161 | 0.42 ± 0.06 | 3.76 ± 1.46 | 14.0 ± 4.3 |
| 2 | −420 | 992 | <1 | NT | 3.25 |
| 3 | −460 | 139 ± 18.3 | 0.79 ± 0.24 | 1.77 ± 0.75 | 4.8 ± 1.4 |
| 4 | −500 | 18.5 ± 3.3 | 0.85 ± 0.35 | 1.20 ± 0.50 | 3.5 ± 0.7 |
| 5 | −132 | 26.1 ± 2.0 | 0.54 ± 0.12 | 0.92 ± 0.21 | 12.8 ± 3.5 |
| 6 | −232 | 1.75 ± 0.10 | 1.33 ± 0.13 | 0.85 ± 0.03 | 48.2 ± 9.0 |
| 7 | −307 | 2.91 ± 0.47 | 2.81 ± 0.16 | 2.03 ± 0.47 | 50.8 ± 3.7 |
| 8 | −352 | 1.56 ± 0.08 | 1.28 ± 0.23 | 2.14 ± 0.56 | 21.2 ± 4.0 |

It is clear from the data of Table 2 that the examples of the cobalt complexes of general formulae (I) to (V) listed in Table 1 include compounds which are active as cytotoxic agents, and which have the additional capability of being selectively toxic to hypoxic tumour cells in vitro.

The present invention therefore also provides pharmaceutical compositions having antitumour activity and comprising at least one compound represented by one of the general formulae (I) to (V), and one or more pharmaceutically-acceptable carriers or diluents.

The present invention further provides a method for treating tumours, and in particular cancers, in a patient, which comprises administering to the patient an antitumour effective amount of at least one compound represented by one of the general formulae (I) to (V).

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against he contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, clorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitabale as unitary dosages for the mammalian subjects to be treated; each unit containing a predetermined therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about 1 to about 30 mg being preferred. Expressed in proportions, the active compound is generally present in from about 0.1 to 400 mg/ml of carrier. In the case of compositions containing supplementary active ingredients, the dosages are determined by reference to the usual dose and manner of administration of the said ingredients.

What is claimed is:

1. A substantially purified compound represented by the general formula (III):

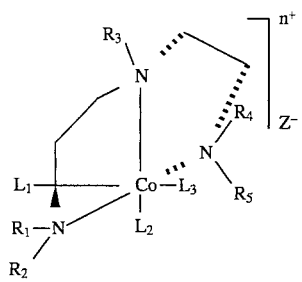

where $R_1$–$R_5$ separately represent H, lower alkyl (optionally substituted with hydroxy and/or amine functions) containing from 1 to 6 carbon atoms, or $CH_2CH_2Cl$, except that two but not more than two of $R_1$–$R_5$ shall represent $CH_2CH_2Cl$ groups in any one molecule; $L_1$–$L_3$ separately represent all possible combinations of $Cl^-$, $NO_2^-$ and $NH_3$ monodentate ligands, or represent a combination of one of these monodentate ligands together with an acetylacetonate bidentate ligand, or collectively represent a tridentate ligand selected from iminodiacetato, N-(Q)iminodiacetato where Q is lower alkyl (optionally substituted with hydroxy and/or amine functions) containing from 1 to 6 carbon atoms, glycylglycinato and 2,6-pyridinedicarboxylato; n is 0 or 1, and, when n=1, $Z^-$ represents $Cl^-$, $Br^-$, $I^-$, $ClO_4^-$, $NO_3^-$, $HCO_3^-$ or any other pharmaceutically-acceptable organic or inorganic counterion.

2. A compound represented by the general formula (III):

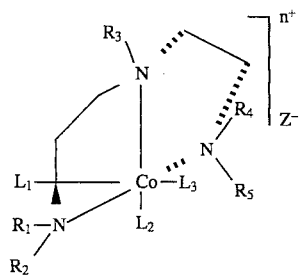

where $R_1$–$R_5$ separately represent H, lower alkyl (optionally substituted with hydroxy and/or amino functions) containing from 1 to 6 carbon atoms, or $CH_2CH_2Cl$, except that not more than two of $R_1$–$R_5$ shall represent $CH_2CH_2Cl$ groups in any one molecule; $L_1$–$L_3$ separately represent all possible combinations of $Cl^-$, $NO_2^-$ and $NH_3$ monodentate ligands, or a combination of one of these monodentate ligands together with an acetylacetonate bidentate ligand or may collectively represent a tridentate ligand; n is 0 or 1, and, when n=1, $Z^-$ represents $Cl^-$, $Br^-$, $I^-$, $ClO_4^-$, $NO_3^-$, $HCO_3^-$ or any other pharmaceutically-acceptable organic or inorganic counterion; and with the proviso that compound is not selected from the group consisting of $[Co(NO_2)_3(Cl$-etoldien)]$, $[Co(NO_2)_2—Cl(Cl$-etoldien)]$ and $[Co(NO_2)_3(dietoldien)]$.

3. The compound of claim 1, or 2 in which said tridente ligand is selected from the group consisting of iminodiacetato, glycylglycinato, 2,6-pyridinedicarboxylate, and N-(Q) iminodiacetato, where Q is a lower alkyl (optionally substituted with hydroxy and/or amino functions) containing from 1 to 6 carbon atoms.

4. A compound of formula (III) according to claim 1, where $L_1$–$L_3$ are $NO_2$—, $R_1$ and $R_2$ are $CH_2CH_2Cl$, $R_3$–$R_5$ are H, and n=0.

5. A process for the preparation of a compound represented by the general formula (III) as defined in claims 1 or 2, which comprises mixing a solution of the sodium salt of the hexanitrocobaltate complex, $Na_3[Co(NO_2)_6]$, with a solution of N',N-bis(2-chloroethyl)-diaethylene triamine mustard ligand, stirring the mixture at a temperature between 0°–40° C. for the appropriate period, and, if desired, substituting one or more of the remaining nitro groups with the appropriate ligand.

6. A pharmaceutical composition having antitumour activity which comprises:

a) at least one compound represented by the general formula III as defined in claim 1, and one or more pharmaceutically-acceptable carriers or diluents.

7. A method for treating tumours in a patient, which comprises administering to the patient an antitumor effective amount of at least one compound represented by the general formula (III) as defined in claim 1.

8. The method of claim 7 in which said tumours are cancers.

* * * * *